United States Patent
Kim et al.

(10) Patent No.: US 11,350,823 B2
(45) Date of Patent: Jun. 7, 2022

(54) ELECTRONIC APPARATUS AND CONTROL METHOD THEREFOR

(71) Applicant: SAMSUNG ELECTRONICS CO., LTD., Suwon-si (KR)

(72) Inventors: Jong-tae Kim, Suwon-si (KR); Yong-ho Kim, Seoul (KR); Jong-hyun Ryu, Suwon-si (KR); Yong-gook Park, Yongin-si (KR); Ae-young Lim, Yongin-si (KR); Hyung-rae Cho, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 51 days.

(21) Appl. No.: 16/091,207

(22) PCT Filed: Mar. 24, 2017

(86) PCT No.: PCT/KR2017/003218
§ 371 (c)(1),
(2) Date: Oct. 4, 2018

(87) PCT Pub. No.: WO2017/175997
PCT Pub. Date: Oct. 12, 2017

(65) Prior Publication Data
US 2019/0110683 A1    Apr. 18, 2019

(30) Foreign Application Priority Data
Apr. 4, 2016  (KR) .................. 10-2016-0040966

(51) Int. Cl.
*A61B 5/00*      (2006.01)
*A61B 5/0205*   (2006.01)
(Continued)

(52) U.S. Cl.
CPC .......... *A61B 5/0006* (2013.01); *A61B 5/0002* (2013.01); *A61B 5/021* (2013.01);
(Continued)

(58) Field of Classification Search
CPC .... A61B 2560/0475; A61B 2562/0219; A61B 2562/0223; A61B 2562/0233;
(Continued)

(56) References Cited

U.S. PATENT DOCUMENTS

| | | | |
|---|---|---|---|
| 7,905,832 B1 * | 3/2011 | Lau ...................... | G16H 50/20 600/300 |
| 9,503,563 B2 | 11/2016 | Jang et al. | |

(Continued)

FOREIGN PATENT DOCUMENTS

| | | |
|---|---|---|
| EP | 0 809 965 | 12/1997 |
| KR | 10-2008-0074306 | 8/2008 |

(Continued)

OTHER PUBLICATIONS

International Search Report for PCT/KR2017/003218, dated Jun. 15, 2017, 4 pages.

(Continued)

*Primary Examiner* — Niketa Patel
*Assistant Examiner* — Vynn V Huh
(74) *Attorney, Agent, or Firm* — Nixon & Vanderhye, P.C.

(57) ABSTRACT

An electronic apparatus according to various embodiments of the present disclosure may comprise: a sensor unit for sensing the movement of the electronic apparatus; a communication unit for communicating with an external apparatus; an input unit for receiving a user input; an output unit for providing information to a user; and a control unit for outputting a message inducing a particular action to the user through the output unit on the basis of medical information (Continued)

of the user and the movement of the electronic apparatus, or controlling the communication unit to transmit information related to the electronic apparatus to an external apparatus.

16 Claims, 8 Drawing Sheets

(51) Int. Cl.
| | |
|---|---|
| A61B 5/021 | (2006.01) |
| A61B 5/024 | (2006.01) |
| A61B 5/11 | (2006.01) |
| G08B 21/04 | (2006.01) |
| G16H 40/63 | (2018.01) |
| G16H 40/67 | (2018.01) |
| H04M 1/72418 | (2021.01) |
| H04M 1/725 | (2021.01) |
| H04W 4/029 | (2018.01) |
| H04W 4/90 | (2018.01) |
| A61B 5/1172 | (2016.01) |
| A61B 5/318 | (2021.01) |
| A61B 5/369 | (2021.01) |
| H04W 4/02 | (2018.01) |
| H04W 4/80 | (2018.01) |
| G16H 20/30 | (2018.01) |
| A61B 5/01 | (2006.01) |
| G06F 1/16 | (2006.01) |
| G06F 3/0488 | (2022.01) |
| H04M 1/72457 | (2021.01) |
| A61B 5/389 | (2021.01) |

(52) U.S. Cl.
CPC .......... *A61B 5/024* (2013.01); *A61B 5/02055* (2013.01); *A61B 5/11* (2013.01); *A61B 5/6802* (2013.01); *A61B 5/746* (2013.01); *A61B 5/7475* (2013.01); *G08B 21/0453* (2013.01); *G16H 40/63* (2018.01); *G16H 40/67* (2018.01); *H04M 1/725* (2013.01); *H04M 1/72418* (2021.01); *H04W 4/029* (2018.02); *H04W 4/90* (2018.02); *A61B 5/1112* (2013.01); *A61B 5/1172* (2013.01); *A61B 5/318* (2021.01); *A61B 5/369* (2021.01); *A61B 5/389* (2021.01); *A61B 5/681* (2013.01); *A61B 5/741* (2013.01); *A61B 5/7435* (2013.01); *A61B 5/7455* (2013.01); *A61B 2560/0475* (2013.01); *A61B 2562/029* (2013.01); *A61B 2562/0219* (2013.01); *A61B 2562/0223* (2013.01); *A61B 2562/0233* (2013.01); *A61B 2562/0247* (2013.01); *A61B 2562/0257* (2013.01); *H04M 2250/12* (2013.01); *H04W 4/027* (2013.01); *H04W 4/80* (2018.02)

(58) Field of Classification Search
CPC .... A61B 2562/0247; A61B 2562/0257; A61B 2562/029; A61B 5/0002; A61B 5/0006; A61B 5/02055; A61B 5/021; A61B 5/024; A61B 5/0402; A61B 5/0476; A61B 5/0488; A61B 5/11; A61B 5/1112; A61B 5/1172; A61B 5/6802; A61B 5/681; A61B 5/741; A61B 5/7435; A61B 5/7455; A61B 5/746; A61B 5/7475; G08B 21/0453; G16H 40/63; G16H 40/67; H04M 1/725; H04M 1/72536; H04M 2250/12; H04W 4/027; H04W 4/029; H04W 4/80; H04W 4/90

USPC ......... 361/679.01–679.3; 340/539.11–539.13
See application file for complete search history.

(56) References Cited

U.S. PATENT DOCUMENTS

| | | | |
|---|---|---|---|
| 2006/0270949 A1* | 11/2006 | Mathie | A61B 5/1117 |
| | | | 600/595 |
| 2008/0312709 A1* | 12/2008 | Volpe | A61B 5/1117 |
| | | | 607/6 |
| 2011/0199178 A1* | 8/2011 | Hatano | G06F 3/038 |
| | | | 340/1.1 |
| 2012/0179020 A1 | 7/2012 | Wekell | |
| 2013/0057696 A1* | 3/2013 | Felt | H04N 7/186 |
| | | | 348/158 |
| 2015/0022338 A1* | 1/2015 | Hwang | G06Q 10/1095 |
| | | | 340/501 |
| 2015/0223541 A1 | 8/2015 | Miller, II | |
| 2015/0223705 A1* | 8/2015 | Sadhu | G01S 19/17 |
| | | | 600/301 |
| 2015/0288797 A1* | 10/2015 | Vincent | H04W 4/90 |
| | | | 455/404.2 |
| 2015/0348389 A1 | 12/2015 | Jang et al. | |
| 2016/0035206 A1* | 2/2016 | Pai | A61B 5/1117 |
| | | | 340/539.12 |
| 2016/0089033 A1 | 3/2016 | Saponas et al. | |
| 2017/0011210 A1 | 1/2017 | Cheong et al. | |

FOREIGN PATENT DOCUMENTS

| | | |
|---|---|---|
| KR | 10-2010-0128439 | 12/2010 |
| KR | 10-2013-0119158 | 10/2013 |
| KR | 10-2015-0061195 | 6/2015 |
| KR | 10-2015-0099430 | 8/2015 |
| KR | 10-2015-0116206 | 10/2015 |
| KR | 10-2015-0136716 | 12/2015 |
| KR | 10-2016-0015142 | 2/2016 |

OTHER PUBLICATIONS

Written Opinion of the ISA for PCT/KR2017/003218, dated Jun. 15, 2017, 11 pages.
Extended European Search Report dated Feb. 4, 2019 in counterpart European Patent Application No. Application No. 17779297.5.
Communication pursuant to Article 94(3) EPC dated Jan. 31, 2022 in counterpart European Patent Application No. 17779297.5.

* cited by examiner

ELECTRONIC APPARATUS AND CONTROL METHOD THEREFOR

This application is the U.S. national phase of International Application No. PCT/KR2017/003218 filed 24 Mar. 2017, which designated the U.S. and claims priority to KR 10-2016-0040966 filed 4 Apr. 2016, the entire contents of each of which are hereby incorporated by reference.

BACKGROUND

Apparatuses and methods consistent with the present disclosure relate to an electronic apparatus and a control method therefor and, more particularly, to an apparatus and method for controlling an electronic apparatus using medical information.

DESCRIPTION OF RELATED ART

Recently, along with development of computer technologies and communication technologies, an electronic apparatus attached to a user body has been developed. The electronic apparatus is referred to as a wearable device. The wearable device is attached to the user body, collects medical information of a user using various sensors, and provides information related to health to the user. In particular, a watch-type wearable device is worn on the user wrist, is capable of detecting a heat rate, skin surface temperature, altitude change, user movement, and the like, and is capable of advantageously and continuously monitor health information of the user. The health information is transmitted to another electronic apparatus or a service via communication and is used to manage user health.

SUMMARY

A wearable device provides an emergency service for checking information of a user state in an emergency to contact a medical team but does not provide information on a stage of the emergency of the user and, thus, a user family and a medical team are not capable of accurately recognize emergency of the user. For the reason, a user does not want an emergency service provided by a conventional wearable device and, thus, there is a problem in that appropriate emergency measure for an emergency patient is delayed.

An electronic apparatus according to an exemplary embodiment of the present disclosure may classify an emergency of a user into stages using medical information of the user and variation of a sensor of the electronic apparatus, which are collected using various sensors and may perform an appropriate operation according to each stage and, thus, may provide a service for each stage of the emergency to the user.

According to an aspect of the present disclosure, an electronic apparatus includes a sensor configured to sense movement of the electronic apparatus, a communicator configured to communicate with an external device, an inputter configured to receive a user input, an outputter configured to provide information to a user, and a controller configured to output a message for guiding a specific operation to the user through the outputter based on medical information of the user and movement of the electronic apparatus or to transmit information related to the electronic apparatus to the external device through the communicator.

According to another aspect of the present disclosure, a method of controlling an electronic apparatus includes receiving medical information of a user, sensing movement of the electronic apparatus, and outputting a message for guiding a specific operation to the user based on the medical information and movement of the electronic apparatus or transmitting information related to the electronic apparatus to an external device.

An electronic apparatus according to an exemplary embodiment of the present disclosure may collect medical information of a user and information on movement of the electronic apparatus through various sensors, may classify an emergency of the user into stages based on the collected information, and may perform an operation corresponding to each stage, thereby providing an appropriate emergency service for the emergency to a user, a user family, and a medical team.

DETAILED DESCRIPTION OF EXAMPLE EMBODIMENTS

The present disclosure will now be described more fully with reference to the accompanying drawings, in which exemplary embodiments of the invention are shown. However, this is not intended to limit the present disclosure to particular modes of practice, and it is to be appreciated that all modification, equivalents, and alternatives that do not depart from the spirit and technical scope of the present disclosure are encompassed in the present disclosure. With regard to the description of the drawings, the same reference numerals denote like elements.

In this disclosure, the expressions "have", "may have", "include" and "comprise", or "may include" and "may comprise" used herein indicate existence of corresponding features (e.g., elements such as numeric values, functions, operations, or components) but do not exclude presence of additional features.

In this disclosure, the expressions "A or B", "at least one of A or/and B", or "one or more of A or/and B", and the like may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used in this disclosure may be used to refer to various elements regardless of the order and/or the priority and to distinguish the relevant elements from other elements, but do not limit the elements. For example, "a first user device" and "a second user device" indicate different user devices regardless of the order or priority. For example, without departing the scope of the present disclosure, a first element may be referred to as a second element, and similarly, a second element may be referred to as a first element.

It will be understood that when an element (e.g., a first element) is referred to as being "(operatively or communicatively) coupled with/to" or "connected to" another element (e.g., a second element), it may be directly coupled with/to or connected to the other element or an intervening element (e.g., a third element) may be present. In contrast, when an element (e.g., a first element) is referred to as being "directly coupled with/to" or "directly connected to" another element (e.g., a second element), it should be understood that there are no intervening element (e.g., a third element).

According to the situation, the expression "configured to" used in this disclosure may be used as, for example, the expression "suitable for", "having the capacity to", "designed to", "adapted to", "made to", or "capable of". The term "configured to" must not mean only "specifically designed to" in hardware. Instead, the expression "a device configured to" may mean that the device is "capable of" operating together with another device or other components. For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

Terms used in this disclosure are used to describe specified embodiments and are not intended to limit the scope of another embodiment. The terms of a singular form may include plural forms unless otherwise specified. All the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal unless expressly so defined in various embodiments of this disclosure. In some cases, even if terms are terms which are defined in this disclosure, they may not be interpreted to exclude embodiments of this disclosure.

An electronic apparatus according to various exemplary embodiments of the present disclosure may be a portable apparatus, for example, a smartphone or a wearable apparatus. The electronic apparatus according to exemplary embodiments of the present disclosure is not limited to the aforementioned apparatuses and may include a new electronic apparatus according to the development of a technology.

Hereinafter, an electronic apparatus according to various exemplary embodiments will be described with reference to the attached drawings. In the specification, the term user may refer to a person who uses an electronic apparatus or a device (e.g., an artificial intelligence electronic apparatus) that uses an electronic apparatus.

Figure 1:
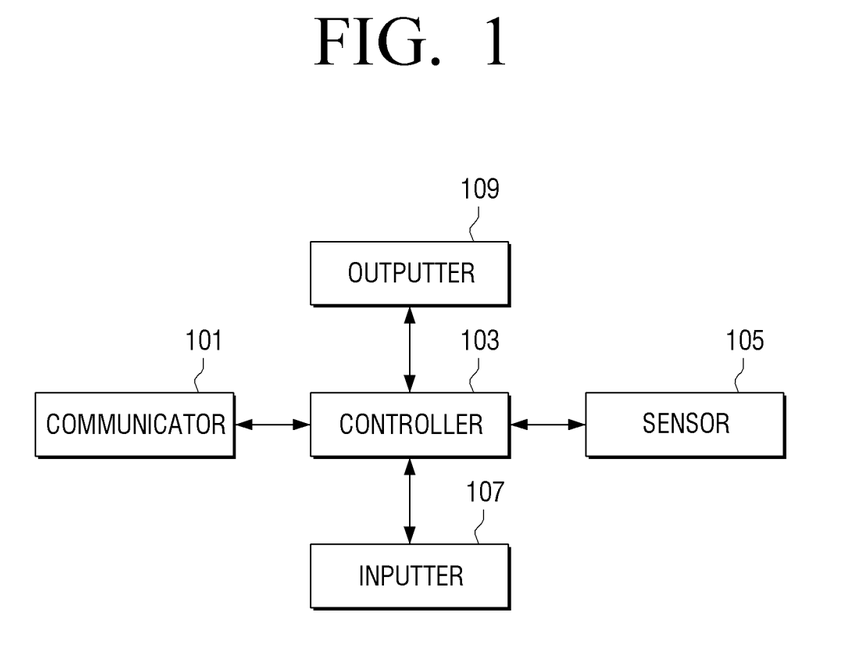
FIG. 1 is a block diagram of an electronic apparatus according to an exemplary embodiment of the present disclosure.

FIG. 1 is a block diagram of an electronic apparatus according to an exemplary embodiment of the present disclosure.

Referring to FIG. 1, the electronic apparatus may include a communicator 101, a controller 103, a sensor 105, an inputter 107, and an outputter 109.

The communicator 101 may communicate with an external device. For example, the communicator 101 may communicate with a server and an electronic apparatus of another user, which is around the electronic apparatus of the user. The electronic apparatus may include a short distance communicator and may communicate with another surrounding electronic apparatus through the short distance communicator. The electronic apparatus may have various form factors. For example, the electronic apparatus may be a patch-type apparatus attached to a user body, an earring-type apparatus worn on a user ear, or a wrist watch-type worn on a user wrist. In this case, when the electronic apparatus has a wearable form factor such as a patch-type, an earring-type, and a wrist watch-type, the electronic apparatus may communicate with a user terminal such as an external smartphone and a personal digital assistant (PDA) using the short distance communicator. In addition, the electronic apparatus may include a long distance communicator and may communicate with a user at a long distance in a $3^{th}$ generation (3G) or long term evolution (LTE) manner.

The communicator may receive medical information from an external device. For example, when the electronic apparatus is embodied as a user terminal such as a smartphone, the electronic apparatus may receive medical information from an external wearable device.

Various examples of the communicator 101 are described in detail with reference to FIG. 2.

The inputter 107 may receive a user input. The inputter 107 may receive a command from a user and may transmit the command to the controller 103. For example, the inputter 107 may be a touch sensor for detection of a user touch, hovering, and/or pen input. In some embodiments, the pen input may be detected using a separate sensor. The inputter 107 may include a physical button. Various examples and shapes of the inputter 107 are described in detail with reference to FIG. 2.

The outputter 109 may provide information to the user. The outputter 109 may provide information to the user in visual, acoustic, and tactile form. The outputter 109 may include, for example, a display, an audio module, and a vibration device. The display may provide visual information to the user. For example, the display may provide information as a text message or a graphic object. As another example, a light emitting diode (LED) may emit light to provide information to the user.

The audio module may provide acoustic information to the user and may output message information using voice. The audio module may include a speaker and an earphone. The speaker may be built in the electronic apparatus. The earphone may be provided in the form of an accessory. The vibration device may provide information to the user using vibration. Various forms of the outputter 109 are described in detail with reference to FIG. 2.

The sensor 105 may sense movement of the electronic apparatus. In some embodiments, the sensor 105 may include a medical sensor and may sense medical information of the user. Various shapes and functions of the sensor 105 are described in more detail with reference to FIG. 2.

The controller 103 may control an overall operation of the electronic apparatus and may output a message for guiding a specific operation to the user based on the medical information of the user and movement of the electronic apparatus through the outputter 109 or may transmit a message and position information of the electronic apparatus to an external apparatus (e.g., an external electronic apparatus or a server) through the communicator 101. The controller 103 may generate medical information based on a signal output from the sensor 105. The controller 103 may determine an external electronic apparatus and server to which the message and the position information are to be transmitted, based on the position information of the electronic apparatus, and may transmit the message and the position information to the external electronic apparatus and the server. For example, upon determining that the user is in an emergency, the controller 103 may control the communicator 101 to search for a rescue center closest to a current position and to transmit a message of the emergency and the position information of the electronic apparatus to the rescue center.

The controller 103 may measure an altitude of the electronic apparatus based on a signal output from the sensor 105. When variation per unit time of the altitude measured by the sensor 105 is greater than a preset value and movement of the electronic apparatus is not detected for a predetermined time, the controller 103 may control the outputter 109 to output a message that asks the user to move. For example, when the user falls from a high place, an abrupt change in altitude may be detected and, in this regard, upon detecting such an abrupt change in altitude from the electronic apparatus, the controller 103 may determine a current situation as a falling accident. Various functions of the controller 103 are described in detail with reference to FIG. 2.

Figure 2:
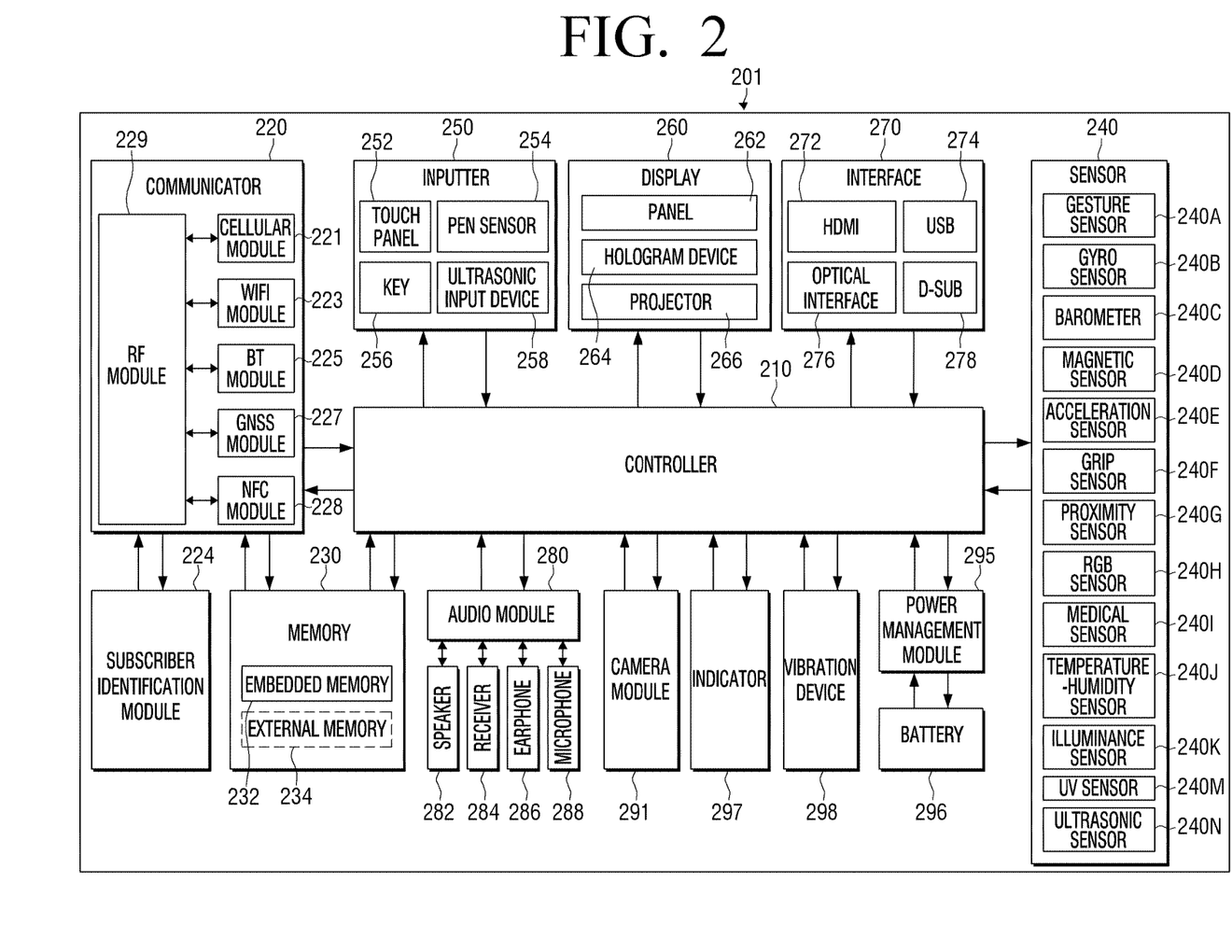
FIG. 2 is a detailed block diagram of an electronic apparatus according to an exemplary embodiment of the present disclosure.

FIG. 2 is a detailed block diagram of an electronic apparatus according to an exemplary embodiment of the present disclosure.

An electronic apparatus 201 may include all or some of the components of the electronic apparatus shown in FIG. 1. The electronic apparatus 201 may include one or more controllers 210 (e.g., application processor (AP)), a communicator 220, a subscriber identification module 224, a memory 230, a sensor 240, an inputter 250, a display 260, an interface 270, an audio module 280, a camera module 291, a power management module 295, a battery 296, an indicator 297, and a vibration device 298.

The controller 210 may drive, for example, an operating system (OS) or an application program to control a plurality of hardware or software components connected to the controller 210 and to perform various data processing and calculation operations. The controller 210 may be embodied as, for example, a system on chip (SoC). According to an exemplary embodiment, the controller 210 may further include a graphic processing unit (GPU) and/or an image signal processor. The controller 210 may include at least some (e.g., a cellular module 221) of the components shown in FIG. 2. The controller 210 may load and process a command or data received from at least one of other components (e.g., a non-volatile memory) to a volatile memory and may store various data in a non-volatile memory.

The communicator 220 may have the same or similar component to the communicator 101 of FIG. 1. The communicator 220 may include the cellular module 221, a WiFi module 223, a Bluetooth module 225, a GNSS module 227 (e.g., a global positioning system (GPS) module, a Glonass module, a Beidou module, or a Galileo module), an NFC module 228, and a radio frequency (RF) module 229.

The cellular module 221 may provide voice call, videotelephony, a text messaging service, an Internet service, or the like through, for example, a network. According to an exemplary embodiment, the cellular module 221 may identify and authenticate the electronic apparatus 201 in a communication network using the subscriber identification module 224 (e.g., a subscriber identification module (SIM) card). According to an exemplary embodiment, the cellular module 221 may perform at least some of functions to be provided by the controller 210. According to an exemplary embodiment, the cellular module 221 may include a communication processor (CP).

Each of the WiFi module 223, the Bluetooth module 225, the GNSS module 227, or the NFC module 228 may include, for example, a processor for processing data transmitted and received through a corresponding module. In some embodiments, at least some (e.g., two or more) of the cellular module 221, the WiFi module 223, the Bluetooth module 225, the GNSS module 227, or the NFC module 228 may be included in one integrated chip (IC) or IC package.

The RF module 229 may transmit and receive, for example, a communication signal (e.g., an RF signal). The RF module 229 may include, for example, a transceiver, a power amp module (PAM), a frequency filter, a low noise amplifier (LNA), an antenna, or the like. According to another exemplary embodiment, at least one of the cellular module 221, the WiFi module 223, the Bluetooth module 225, the GNSS module 227, or the NFC module 228 may transmit and receive an RF signal through a separate RF module.

The subscriber identification module 224 may include, for example, a card including a subscriber identification module and/or an embedded SIM and may include unique identification information (e.g., integrated circuit card identifier (ICCID)) or subscriber information (e.g., international mobile subscriber identity (IMSI)).

The memory 230 (e.g., a memory 130) may include, for example, an embedded memory 232 or an external memory 234. The embedded memory 232 may include at least one of, for example, a volatile memory (e.g., a dynamic random access memory (RAM) (DRAM)), a static RAM (SRAM), or a synchronous dynamic RAM (SDRAM)), a non-volatile memory (e.g., a one time programmable read only memory (ROM) (OTPROM), a programmable ROM (PROM), an erasable and programmable (ROM) (EPROM), an electrically erasable and programmable ROM (EEPROM), a mask ROM, a flash ROM, a flash memory (e.g., a NAND flash or a NOR flash), a hard drive, or a solid state drive (SSD)).

The external memory 234 may include a flash drive (flash drive, for example, a compact flash (CF), a secure digital (SD), a micro secure digital (Micro-SD), a mini secure digital (Mini-SD), an extreme digital (xD), a MultiMedia-Card (MMC), a memory stick, or the like. The external memory 234 may be physically and/or physically connected to the electronic apparatus 201 through various interfaces.

The sensor 240 may measure, for example, a physical quantity, or may detect an operation state of the electronic apparatus 201 and may convert the measured or detected information into an electronic signal. The sensor 240 may include at least one of, for example, a gesture sensor 240A, a gyro sensor 240B, a barometer 240C, a magnetic sensor 240D, an acceleration sensor 240E, a grip sensor 240F, a proximity sensor 240G, a color sensor 240H (e.g., a red, green, blue (RGB) sensor), a medical sensor 240I, a temperature-humidity sensor 240J, an illuminance sensor 240K, or an ultra violet (UV) sensor 240M, or an ultrasonic sensor 240N. Additionally or alternatively, the sensor 240 may include, for example, an E-nose sensor, an electromyography (EMG) sensor, an electroencephalogram (EEG) sensor, an electrocardiogram (ECG) sensor, an infrared (IR) sensor, an iris scan sensor, and/or a finger scan sensor. The sensor

240 may further include a control circuit for control of one or more sensors included in the sensor 240. In some embodiments, the electronic apparatus 201 may further include a processor configured to control the sensor 240, as a portion of the controller 210 or separately, to control the sensor 240 when the controller 210 is in a sleep state.

The inputter 250 may include, for example, a touch panel 252, a (digital) pen sensor 254, a key 256, or an ultrasonic input device 258. The touch panel 252 may use at least one of, for example, an electrostatic method, a pressure sensitive method, an infrared method, or an ultrasonic method. The touch panel 252 may further include a control circuit. The touch panel 252 may further include a tactile layer to provide a tactile reaction to a user.

The (digital) pen sensor 254 may be, for example, a portion of a touch panel or may include a separate recognition sheet. The key 256 may include, for example, a physical button, an optical key, or a keypad. The ultrasonic input device 258 may detect ultrasonic waves generated from an input device and may also verify data corresponding to the detected ultrasonic waves through a microphone (e.g., a microphone 288).

The display 260 (e.g., a display 160) may include a panel 262, a hologram device 264, or a projector 266. The panel 262 may be, for example, flexibly or transparently embodied or may be embodied to be wearable. The panel 262 may be configured as one module with the touch panel 252. The hologram device 264 may show a stereoscopic image into a space using interference of light. The projector 266 may project light to a screen and may display an image. The screen may be positioned inside or outside, for example, the electronic apparatus 201. According to an exemplary embodiment, the display 260 may further include a control circuit for control of the panel 262, the hologram device 264, or the projector 266.

The interface 270 may include, for example, a high-definition multimedia interface (HDMI) 272, a universal serial bus (USB) 274, an optical interface 276, and a D-subminiature (D-sub) 278. The interface 270 may be included in, for example, the communicator 101 shown in FIG. 1. Additionally or alternatively, the interface 270 may include, for example, a mobile high-definition link (MHL) interface, a secure digital (SD) card/multi-media card (MMC) interface, or an infrared data association (IrDA) standard interface.

The audio module 280 may convert, for example, a sound and electronic signal in bi-directions. The audio module 280 may process sound information input or output through, for example, a speaker 282, a receiver 284, an earphone 286, the microphone 288, or the like.

The camera module 291 may be, for example, a device for capturing a still image or a video image and, according to an exemplary embodiment, may include one or more image sensors (e.g., a front sensor or a rear sensor), a lens, an image signal processor (ISP), a flash (e.g., an LED or a xenon lamp), or the like.

The power management module 295 may manage, for example, power of the electronic apparatus 201. According to an exemplary embodiment, the power management module 295 may include a power management integrated circuit (PMIC), a charger integrated circuit (IC), the battery 296, or a battery or a fuel gauge. The PMIC may use a wired and/or wireless charging method. The wireless charging method may include, for example, a magnetic resonance method, an electromagnetic inductive coupling method, an electromagnetic wave method, or the like and may further use an additional circuit for wireless charging, for example, a coil loop, a resonance circuit, a rectifier, or the like. The battery gauge may measure, for example, the remaining amount of the battery 296, or a voltage, current, or temperature during charging. The battery 296 may include, for example, a rechargeable battery and/or a solar battery.

The indicator 297 may display a specific state of the electronic apparatus 201 or a portion thereof (e.g., the controller 210), for example, a booting state, a message state, a charge state, or the like. The vibration device 298 may convert an electronic signal into mechanical vibration and may generate vibration, a haptic (tactile) effect, or the like. Although not shown, the electronic apparatus 201 may include a processing apparatus (e.g., GPU) for supporting a mobile TV. The processing apparatus for supporting the mobile TV may process media data according to standard, for example, digital multimedia broadcasting (DMB), digital video broadcasting (DVB), mediaFlo™, or the like.

Each of the component stated in the present specification may be configured as one or more components and a term of a corresponding component may be changed depending on a type of an electronic apparatus. In various exemplary embodiments, the electronic apparatus may include at least one of the components stated in the present specification and some of the components may be omitted or additional other components may be added. In addition, some of components of the electronic apparatus according to various exemplary embodiments of the present disclosure may be combined to configure one entity and may perform functions of corresponding components in the same way prior to being combined.

Figure 3:
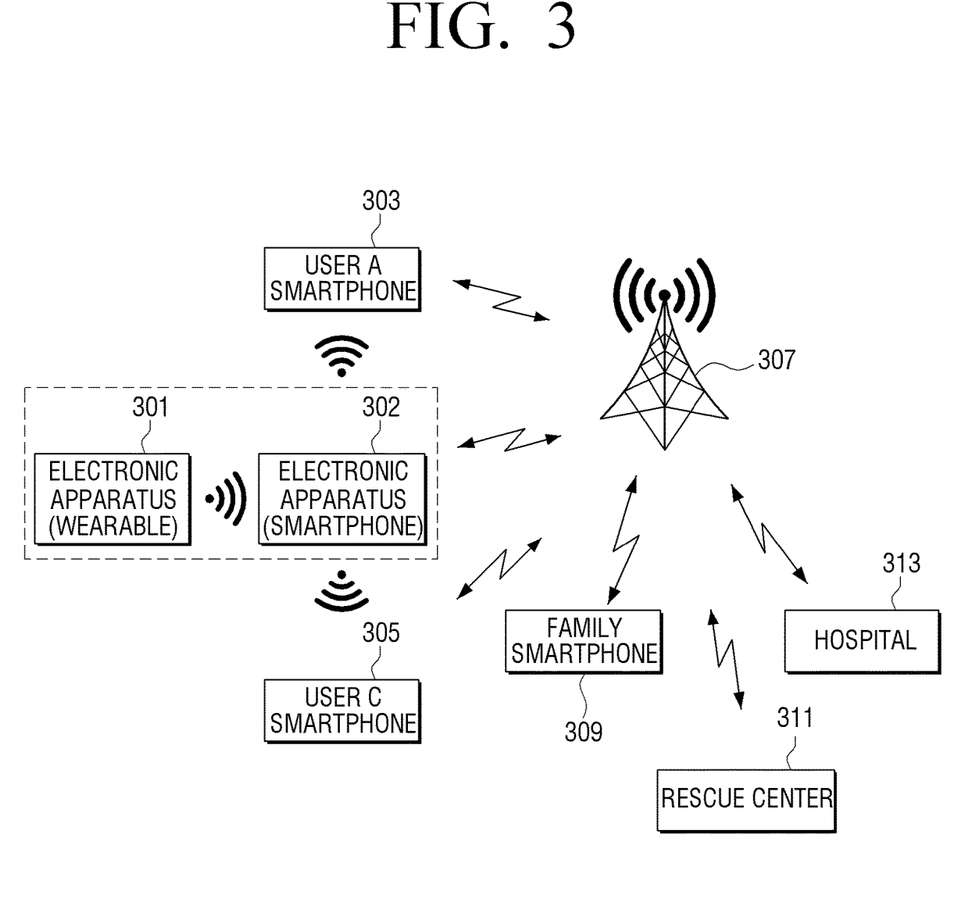
FIG. 3 is a diagram showing a configuration of a system of an electronic apparatus according to an exemplary embodiment of the present disclosure.

FIG. 3 is a diagram showing a configuration of a system of an electronic apparatus according to an exemplary embodiment of the present disclosure.

Referring to FIG. 3, an electronic apparatus 301 may be a wearable device. The wearable device shown in FIG. 3 may include a sensor, a communicator, an inputter, an outputter, and a communicator. A shape and function of the sensor, the communicator, the inputter, the outputter, and the communicator are the same as in the description given with reference to FIGS. 1 and 2 and they perform the same function and, thus, a detailed description thereof is omitted.

The electronic apparatus 301 may include a short distance communicator and a long distance communicator. The electronic apparatus 301 may transmit and receive data to and from the electronic apparatus 302 using the short distance communicator. An electronic apparatus 302 may be, for example, a smartphone. The electronic apparatus 301 and the electronic apparatus 302 may be electronic apparatuses that are carried by the same user and the electronic apparatus 301 and the electronic apparatus 302 may be operatively associated with each other. For example, when the electronic apparatus 302 receives a text message, the text message may be displayed on a display of the electronic apparatus 301.

The electronic apparatus 301 may be worn on a user body to sense a medical signal of the user. For example, the electronic apparatus 301 may be a wrist watch-type apparatus worn on a user wrist. The medical sensor included in the electronic apparatus 301 may sense the user medical signal to output an electronic signal and the electronic apparatus 301 may generate medical information based on the user medical signal. The medical information may be, for example, heart rate, pulse rate, respiration rate, blood pressure, and body temperature.

The sensor of the electronic apparatus 301 may detect movement of the electronic apparatus 301. The sensor of the electronic apparatus 301 may include an altitude sensor and may measure an altitude of a point where the user is currently positioned, using the altitude sensor. The electronic apparatus 301 may determine whether the user falls to the ground based on a signal output from the altitude sensor. That is, when the user falls to the ground, the electronic apparatus 301 worn on the user body may output an electronic signal depending on an altitude of the electronic apparatus through the altitude sensor, and a controller may identify that the altitude is abruptly changed from the electronic signal and may output a message (e.g., emergency message) based on the abrupt change. The electronic apparatus 301 may transmit user message and user position information to a smartphone that is electronic apparatuses 303 and 305 of other surrounding users via short distance wireless communication. In addition, the electronic apparatus 301 may transmit a message to a base station 307 via long distance wireless communication and the base station 307 may transmit a message to a smartphone 309 of a user family, a hospital server 313, and a rescue center 311.

The electronic apparatus 301 may determine a type of a message to be output, based on a signal output from the sensor. The electronic apparatus 301 may receive a user input based on the message and may output other messages to the user based on the user input. In addition, the electronic apparatus 302 may determine whether a message for asking for help is transmitted to a surrounding electronic apparatus or a message for asking for help is transmitted to the smartphone 309 of a user family, the rescue center 311, the hospital 313, and the like, based on the user input received based on the message.

In some embodiments (e.g., when the electronic apparatus 301 is not capable of performing long distance communication), the electronic apparatus 301 may transmit sensed information, for example, medical information and altitude information of the user to the electronic apparatus 302. That is, the electronic apparatus 301 may transmit information sensed by the electronic apparatus 301 to the electronic apparatus 302 via short distance wireless communication. The electronic apparatus 302 may output a message based on the sensing information received from the electronic apparatus 301 or may transmit a message to the electronic apparatuses 303 and 305 to other surrounding users via short distance wireless communication. In addition, the electronic apparatus 302 may transmit a message to the base station 307 via long distance communication and the base station 307 may transmit a message to the smartphone 309 of the user family, the hospital server 313, and the rescue center 311.

The electronic apparatus 302 may receive a user input in a state in which a message for asking for the user input and may output another message to the user or may transmit a message for asking help to a surrounding electronic apparatus, based on the user input. In addition, the electronic apparatus 302 may transmit a message for asking help to the smartphone 309 of the user famility, the rescue center 311, and the hospital.

The electronic apparatus 302 may further include a microphone and may determine whether the user is in an emergency based on voice input through the microphone. For example, when the electronic apparatus outputs a message "If you are OK, say I am OK" and receives voice "I am OK" from a user through the microphone, the electronic apparatus 302 may determine that the user is not in an emergency. When the electronic apparatus does not receive any input from the user through the microphone, the electronic apparatus may determine an emergency.

When the outputter includes a touchscreen, the electronic apparatus may receive a user input through the touchscreen and may determine whether the user is in an emergency based on the user input. For example, the electronic apparatus may display a button on the touchscreen, may output a message for allowing the user to touch the button and, then, upon receiving a touch input from the user, the electronic apparatus may determine that the user is not in an emergency and, when there is no touch input from the user, the apparatus may determine that the user is in an emergency.

Figure 4A:
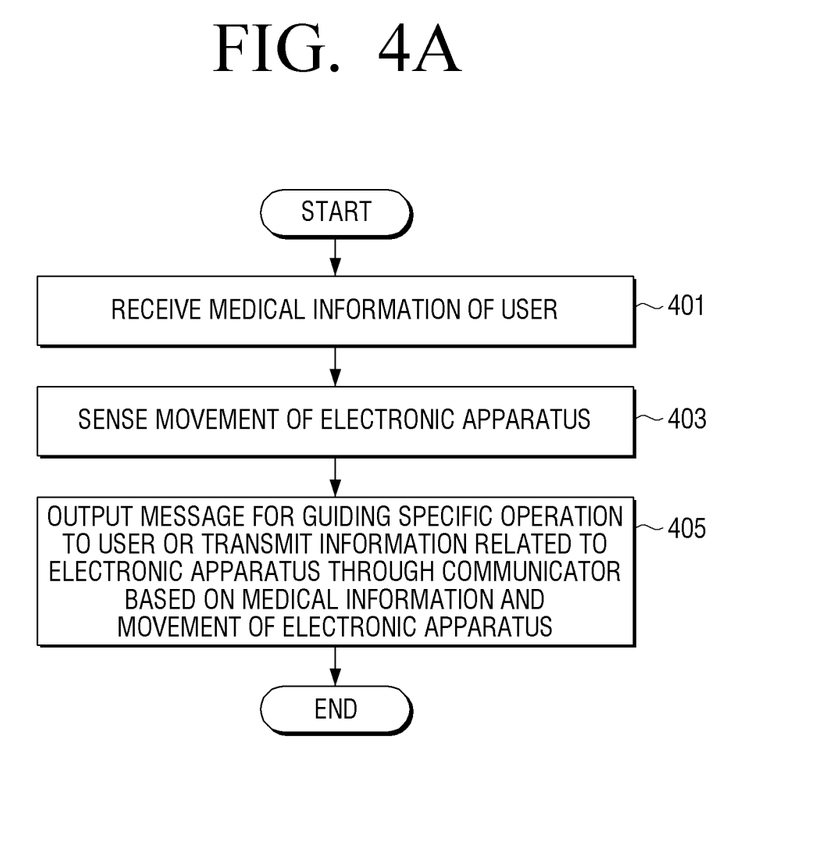
FIGS. 4A and 4B are flowcharts of an operation method of an electronic apparatus according to an exemplary embodiment of the present disclosure.
Figure 4B:
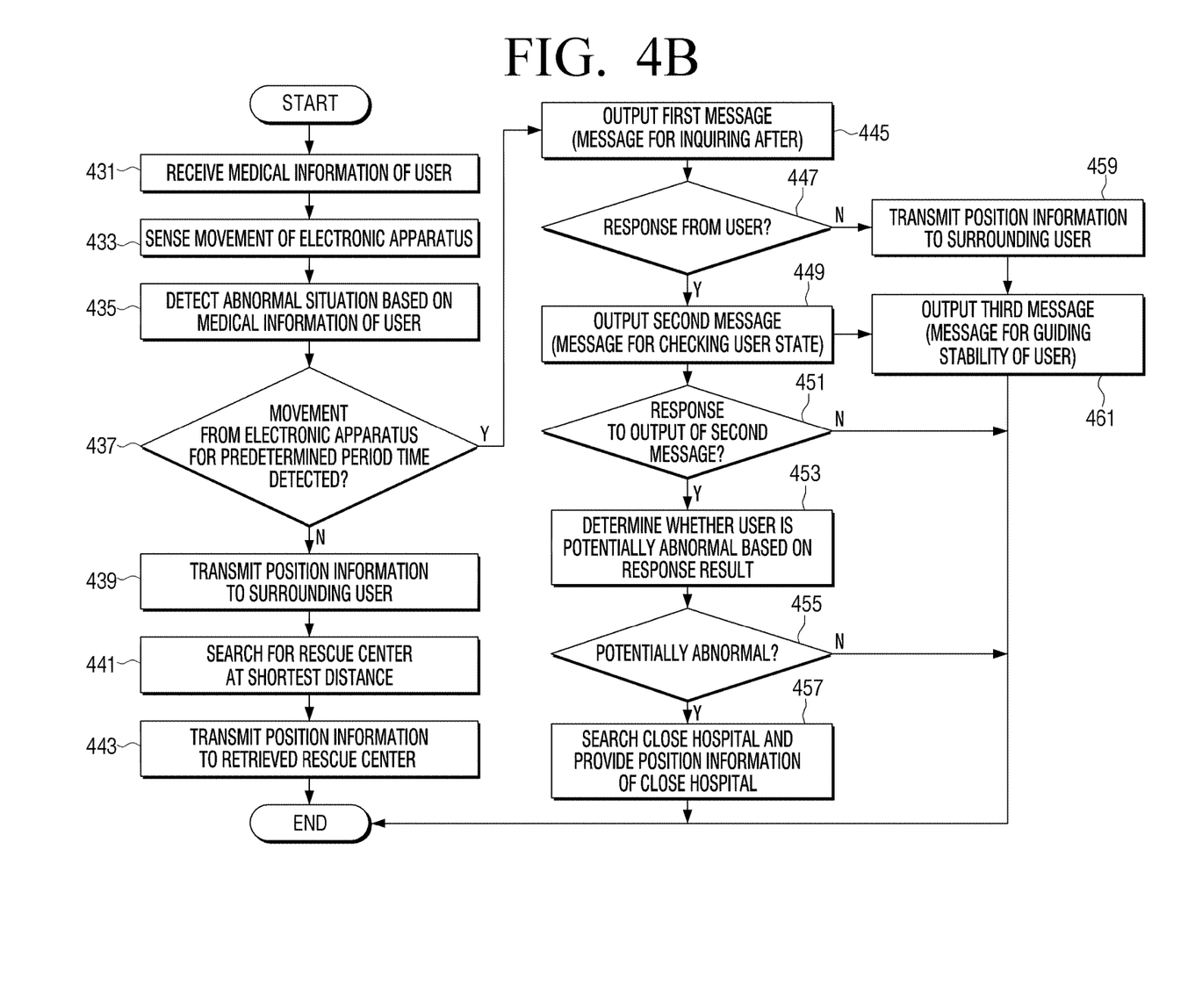

FIGS. 4A and 4B are flowcharts of an operation method of an electronic apparatus according to an exemplary embodiment of the present disclosure.

Referring to FIG. 4A, the electronic apparatus 301 may receive medical information of a user in operation 401. The electronic apparatus 301 may be attached to or mounted on a user body. For example, the electronic apparatus 301 may be a wrist watch-type wearable device. In particular, the electronic apparatus 301 may include a medical sensor and may receive the medical information (e.g., a heart rate, a pulse rate, blood pressure, or body temperature) of the user through the medical sensor. The electronic apparatus may analyze the medical information of the user to determine whether the user is in a normal state or an abnormal state. For example, when a heart rate of the user is higher or lower than a normal value, the electronic apparatus 301 may determine that the user is in an abnormal state.

The electronic apparatus 301 may detect movement of the electronic apparatus 301 in operation 403. In particular, upon determining that the user is in an abnormal state in operation 401, the electronic apparatus 301 may detect movement of the electronic apparatus 301 through the sensor to determine whether movement of the user is present. When movement is not detected in the electronic apparatus for a predetermined period of time, the electronic apparatus 301 may determine that the user is in an abnormal state. In detail, the electronic apparatus 301 may detect movement of the electronic apparatus based on a signal output from the sensor. The sensor may include an acceleration sensor and the electronic apparatus 301 may analyze a signal output from the acceleration sensor to determine whether the electronic apparatus is moved.

The electronic apparatus 301 may output a message for guiding a specific operation to the user or may transmit information related to the electronic apparatus 301 through a communicator based on the medical information and movement of the electronic apparatus in operation 405. Upon determining that the user is in an emergency as a determination result of the medical information of the user and the movement of the electronic apparatus 301, the electronic apparatus 301 may output a message for asking the user to move to determine a stage of an emergency of the user. The stage of the emergency may be classified into, for example, first to third stages and the first-stage emergency is the most serious situation in which the user is unconscious, movement is not detected, and prompt emergency measure is required. When the medical information of the user is in a range of an abnormal state and user movement is not detected for a predetermined time period, the electronic apparatus 301 may determine a current situation as the first-stage emergency, may search for the rescue center 311 at a close distance, and may transmit position information of the user to the rescue center 311.

The second-stage emergency is a situation in which the user is determined to be slightly conscious and, when the medical information of the user is in a range of an abnormal state and user movement is detected, the electronic apparatus 301 may output a message for inquiring after the user. In this case, the electronic apparatus 301 may output voice, for example, "Are you OK?" or may display this through a display. When the user does not respond to the output message, the electronic apparatus 301 may determine a current situation as the second-stage emergency. The electronic apparatus 301 may transmit position information of the user and a message for asking for rescue to the electronic apparatuses 303 and 305 of surrounding users through a communicator in the second-stage emergency. The electronic apparatus 301 may transmit the message for asking for help and the user position information to the electronic apparatuses 303 and 305 of surrounding users via short distance wireless communication. The electronic apparatus 301 may output a message on an operation to be taken by the user to the user and may ask the user to take a stable posture. For example, the electronic apparatus 301 may output a message "Don't move and lie flat" to the user.

The third-stage emergency is a situation in which the electronic apparatus 301 determines that the user has a relatively slight problem. When the medical information of the user is in a range of an abnormal state, movement is detected from the electronic apparatus 301, and a user input is received in response to the message output from the electronic apparatus 301, the electronic apparatus 301 may determine a current state as the third-stage emergency. Upon receiving a user input in response to a message for inquiring after the user, the electronic apparatus 301 may output a second message. When a first message is output and, then, the user performs an operation related to the first message, the electronic apparatus 301 may output the second message. The second message may include, for example, a question for checking a user state. The second message may be provided in the form of a survey. Upon receiving a response to the second message from the user, the electronic apparatus 301 may determine whether the user is potentially abnormal based on the response result and, upon determining that the user is potentially abnormal, the electronic apparatus 301 may determine a current state as the third-stage emergency and may provide information on the close hospital 313 to the user to guide the user to the close hospital 313.

With reference to FIG. 4B, an operating method of the electronic apparatus 301 is described in detail. Operations 431 and 433 are the same as operations 401 and 403 of FIG. 4A and, thus, a detailed description thereof is not given here. The electronic apparatus 301 may detect an abnormal situation based on the medical information of the user in operation 435. In detail, the electronic apparatus 301 may detect an abnormal situation of the user based on a signal output from the sensor. The sensor may include a medical sensor and may sense the medical information of the user, for example, a heart rate, a pulse rate, blood pressure, and body temperature to output an electronic signal based on the sensed information. The electronic apparatus 301 may generate medical information based on the electronic signal output from the sensor and may identify a current state of the user. For example, when a heart rate, a pulse rate, blood pressure, and body temperature of the user is out of a normal range, the electronic apparatus 301 may determine that the user is in an abnormal situation. The electronic apparatus 301 may detect the abnormal situation of the user and may check movement of the user. The movement of the user may be determined by determining whether movement is detected from the electronic apparatus 301 that is worn or carried by the user. The electronic apparatus 301 may determine whether movement is detected from the electronic apparatus for a predetermined period time in operation 437.

In detail, the electronic apparatus 301 may analyze an output value of the acceleration sensor included in the sensor to determine whether the electronic apparatus 301 is moved. Upon determining that the electronic apparatus 301 is not moved for a predetermined time period, the electronic apparatus 301 may transmit current position information to the user to surrounding users in operation 439. The electronic apparatus 301 may acquire position information of the electronic apparatus 301 using a GPS receiver included in the electronic apparatus 301. In some embodiments (e.g., when the electronic apparatus 301 does not include a GPS receiver), the electronic apparatus 301 may receive the position information from another electronic apparatus (e.g., the electronic apparatus 302 and the base station 307). The electronic apparatus 301 may search for the surrounding electronic apparatuses 303 and 305 to search for a surrounding user. The electronic apparatus 301 may search for the electronic apparatuses 303 and 305 of a surrounding user via short distance wireless communication. For example, the electronic apparatus 301 may search for the surrounding electronic apparatuses 303 and 305 via Bluetooth or WiFi communication and may transmit the user position information and a rescue request message to the retrieved electronic apparatuses 303 and 305. The rescue request message may be preset by the user or may preset by a manufacturer of the electronic apparatus.

The electronic apparatus 301 may search for the rescue center 311 at a shortest distance in operation 441. The electronic apparatus 301 may determine the rescue center 311 at the shortest distance based on position information of the electronic apparatus 301. In detail, when the rescue center is retrieved, the electronic apparatus 301 may calculate a distance between a position of the electronic apparatus 301 and a position of the rescue center and may determine the rescue center 311 at a shortest distance The electronic apparatus 301 may transmit the position information of the user and the rescue request message to the rescue center 311 retrieved in operation 443. When the rescue center 311 at a shortest distance is determined, the electronic apparatus 301 may transmit the position information of the electronic apparatus 301 and the rescue request message to the rescue center 311 retrieved via long distance communication.

Upon detecting movement from the electronic apparatus 301 in operation 437, the electronic apparatus 301 may determine that the user moves and may output the first message in operation 445. The first message may be a message for inquiring after the user. For example, the first message may be an expression such as "Are you OK?" or "Are you all right?". The electronic apparatus 301 may display the first message on a display. Alternatively, the electronic apparatus 301 may output the first message via voice. Alternatively, the electronic apparatus 301 may output the first message via vibration. The first message may be a message preset by a user. Alternatively, the first message may be preset during manufacture of when the electronic apparatus 301 or may be provided. The first message may be a message for asking for a response of a user. Alternatively, the first message may be a message for asking the user to perform a specific operation. For example, the first message may ask the user to perform a voice input "Answer if you ok". Alternatively, the first message may ask the user to perform a specific operation such as "Raise the hand with wearable device thereon".

The electronic apparatus 301 may check whether a response is present from the user in operation 447. Upon receiving a response corresponding to the first message from the user within a predetermined time period after the first message is output, the electronic apparatus 301 may output the second message in operation 449. The second message may be a message for checking a user state and may include a plurality of questions. The second message may include a plurality of survey forms and the electronic apparatus 301 may analyze a response input by the user to determine the user state. The second message may be provided in the form of visual, acoustic, and tactile form in the same way as in operation 445.

When there is a response to the second message from the user in a state in which the second message is input in operation 451, the electronic apparatus 301 may determine whether the user is potentially abnormal based on the response result in operation 453. The second message may be provided in the form of a questionnaire including a plurality of questions. The electronic apparatus 301 may analyze a response to the survey to determine whether the user is potentially abnormal in operation 455. That is, the electronic apparatus 301 may determine whether the user is potentially abnormal based on the input received from the user in a state in which the second message is output. In detail, the electronic apparatus 301 may determine whether the user is abnormal based on the number of answers that are received from the user in a state in which the second message is output.

For example, when a questionnaire includes 10 questions and a user checks three answers or less, the electronic apparatus 301 may determine that the user is potentially abnormal. Upon determining that the user is potentially abnormal, the electronic apparatus 301 may search for the close hospital 313 and may provide position information of the close hospital 313 to the user. The electronic apparatus 301 may search for one hospital or more based on position information of the electronic apparatus 301 and may calculate a distance between the retrieved hospital and the electronic apparatus 301 to determine the closest hospital 313. Determining the closest hospital 313, the electronic apparatus 301 may display position information of the hospital 313 on a display or may output the position information via voice.

When there is no response from the user in operation 447, the electronic apparatus 301 may transmit the position information to the electronic apparatuses 303 and 305 of a surrounding user in operation 459. An operation of transmitting the position information to the surrounding electronic apparatuses 303 and 305 by the electronic apparatus 301 is the same as operation 439 and a detailed description thereof is omitted here.

The electronic apparatus 301 may output a third message in operation 461. The third message may be provided using visual, acoustic, and tactile senses, or the like. The third message may include information for guiding stability of the user. That is, the third message may include information for asking the user to perform a specific operation.

Figure 5:
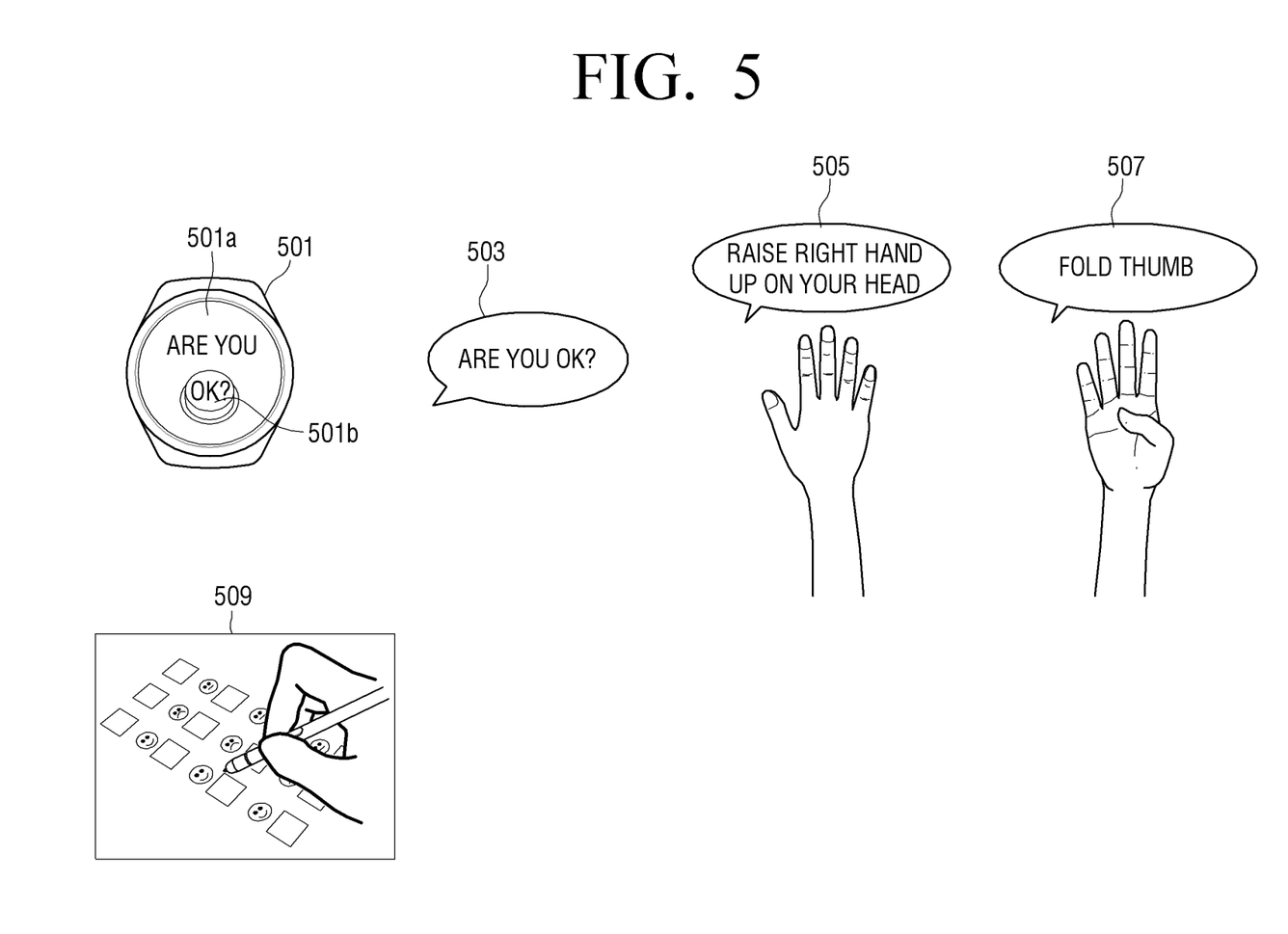
FIG. 5 is a diagram showing an example of a message provided to a user by an electronic apparatus according to an exemplary embodiment of the present disclosure.

FIG. 5 is a diagram showing an example of a message provided to a user by the electronic apparatus 301 according to an exemplary embodiment of the present disclosure.

FIG. 5 shows the message provided by the electronic apparatus 301 to check a user state. As described with reference to FIGS. 4A and 4B, the electronic apparatus 301 may output the first message and the second message to inquire after the user. The electronic apparatus 301 may display first messages 501a and 501b on a display 501 to inquire after the user. The display 501 may detect a touch input. A condition in which the first message is output is the same as in the description given with reference to FIGS. 4A and 4B and, thus, a detailed description thereof is omitted here. The electronic apparatus 301 may output the first message based on the medical information and movement of the electronic apparatus 301. The electronic apparatus 301 may display the message 501a for inquiring after the user and the message 501b for asking for a user response on the display 501. The electronic apparatus 301 may receive a user input through the message 501b in a state in which the message 501a for inquiring after the user is displayed. The message 501b may include a text and a graphic object. For example, the message 501b may include a word or button for guiding a user input. A position at which a word 501b or button for guiding a user input is displayed may be variable.

The first message may include the message 501a for asking the user a question and a graphic object 501b for receiving a user input. The graphic object 501b may include a text for guiding a response from the user. The first message may be provided as a voice output 503. For example, the electronic apparatus 301 may output a message 503 via voice. The voice output 503 may be provided to the user through a speaker included in the electronic apparatus 301. The voice output 503 may be provided to a earphone worn by the user via short distance wireless communication such as Bluetooth. Alternatively, the voice output 503 may be provided to an earphone through an earphone jack.

The first message may include information for asking the user to perform a specific operation. The electronic apparatus 301 may output the first message and may detect movement of the electronic apparatus 301 through the sensor. For example, the electronic apparatus 301 may output a message "Raise the right hand up on your head 505" and may detect movement of the electronic apparatus 301. Alternatively, the electronic apparatus 301 may output a message "Fold the thumb 507" and may detect movement of the electronic apparatus 301. In detail, the electronic apparatus 301 may output the first message and may determine movement of the electronic apparatus 301 based on a signal output from the acceleration sensor.

The electronic apparatus 301 may output a second message to check a user state. A condition and shape for outputting the second message are the same as in the description given with reference to FIGS. 4A and 4B and, thus, a detailed description thereof is omitted here. The second message may include a questionnaire 509 and may be displayed by the display 501. The second message may include a plurality of questions and may include a message for asking the user to do a perceptual behavior or a cognitive behavior.

Figure 6:
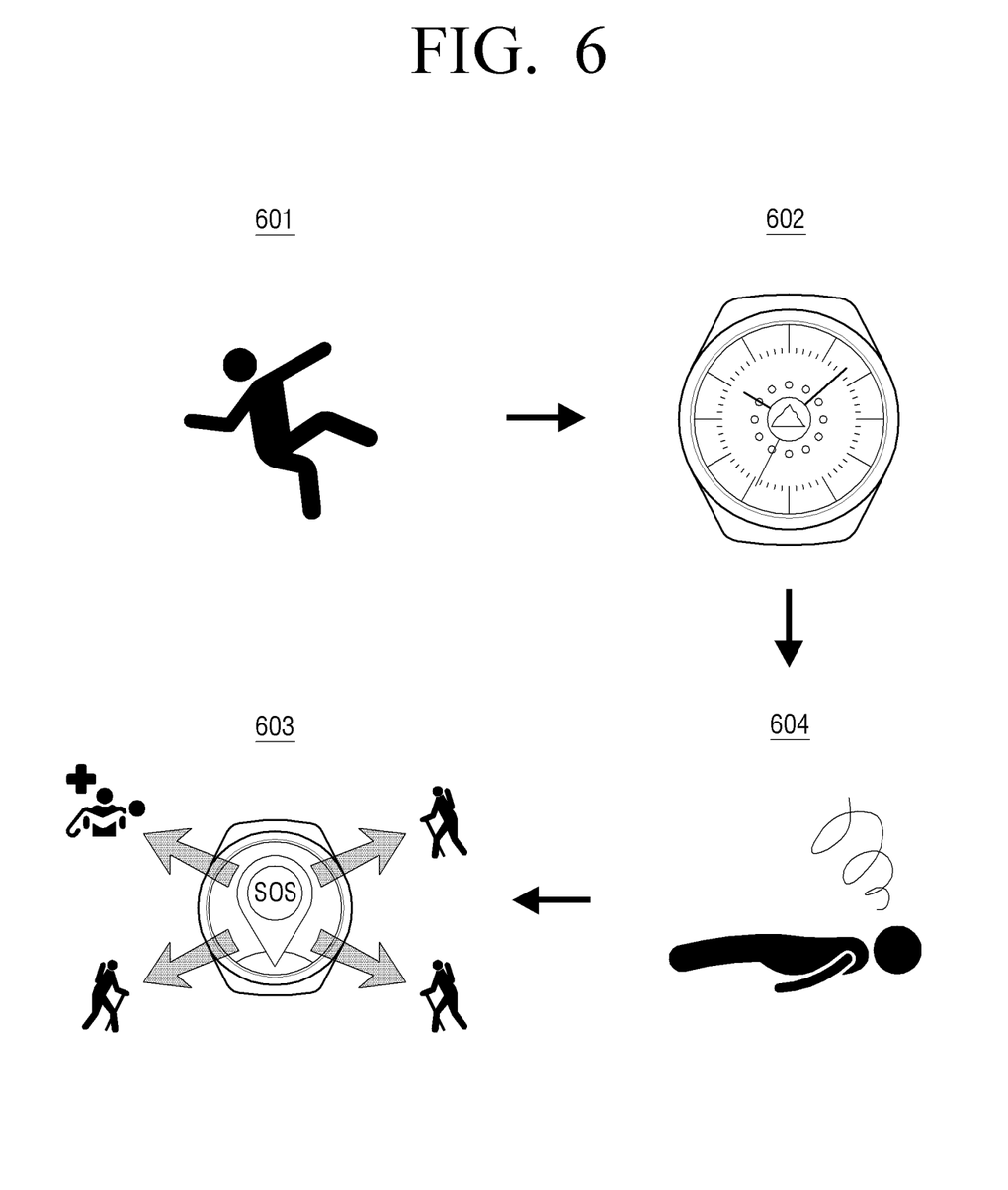
FIG. 6 is a diagram showing an example of an operation of an electronic apparatus according to an exemplary embodiment of the present disclosure.

FIG. 6 is a diagram showing an example of an operation of the electronic apparatus 301 according to an exemplary embodiment of the present disclosure.

Referring to FIG. 6, when an accident occurs, for example, the user falls to the ground during mountain climbing in operation 601, the electronic apparatus 301 may detect an abrupt change in a user altitude through the sensor in operation 602. The electronic apparatus 301 may detect an abrupt change in a user heart rate through the sensor. In detail, the electronic apparatus 301 may check a heart rate of the user based on a signal output from a heart rate sensor and may determine whether the heart rate of the user is abruptly changed. In particular, when a heart rate is checked at a frequency corresponding to a predetermined time period and the heart rate is more greatly changed than a previous heart rate, the electronic apparatus 301 may determine that the user is in an abnormal situation.

The electronic apparatus 301 may determine that the user is in an abnormal situation based on an altitude of the electronic apparatus 301 and the medical information of the user and may check whether user movement is detected. The electronic apparatus 301 may determine whether the user is moved according to movement of the electronic apparatus 301. The electronic apparatus 301 may determine whether the electronic apparatus 301 is moved based on a signal output from the acceleration sensor in operation 603.

Upon determining that the altitude of the electronic apparatus 301 and the user heart rate are abruptly changed, the electronic apparatus 301 may check a signal output from the sensor and may determine whether the electronic apparatus 301 is moved. When the electronic apparatus 301 is not moved, the electronic apparatus 301 may determine that the user is in an first-stage emergency and may perform an operation corresponding thereto in operation 604. In the first-stage emergency, the electronic apparatus 301 may transmit position information of the user to other surrounding electronic apparatuses 303 and 305. Alternatively, the electronic apparatus 301 may transmit user position information to the rescue center 311 at a shortest distance. A detailed operation performed by the electronic apparatus 301 in the first-stage emergency is the same as in the description given with reference to FIGS. 4A and 4B and, thus, a detailed description thereof is omitted here.

Figure 7:
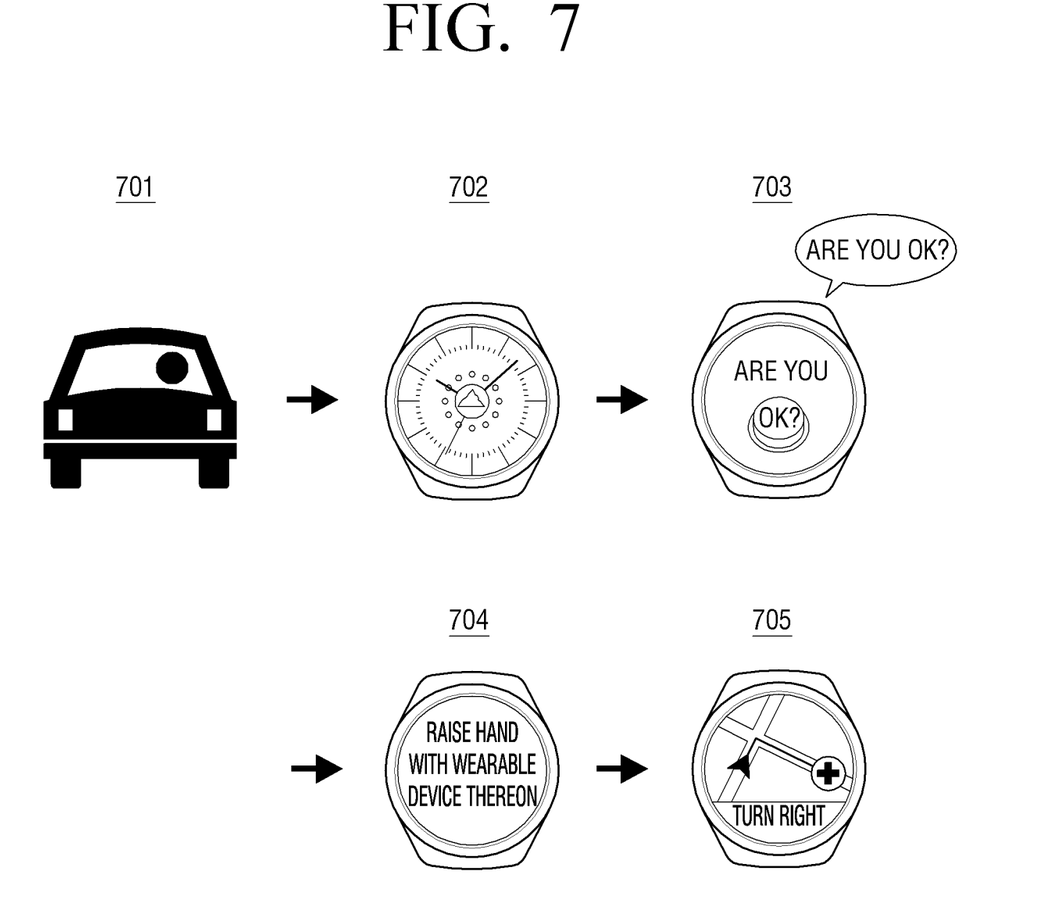
FIG. 7 is a diagram showing an example of an operation of an electronic apparatus according to another exemplary embodiment of the present disclosure.

FIG. 7 is a diagram showing an example of an operation of the electronic apparatus 301 according to another exemplary embodiment of the present disclosure.

Referring to FIG. 7, the electronic apparatus 301 may detect that a user heart rate is abnormal during driving in operation 701. The electronic apparatus 301 may sense the user heart rate through the medical sensor. When a difference between a current measured heart rate and a previously measured heart rate is equal to or greater than a preset value, the electronic apparatus 301 may determine that the heart rate is not normal. Upon determining that the user heart rate is not normal, the electronic apparatus 301 may check whether user movement is detected. The user movement may be determined by checking movement of the electronic apparatus 301. When movement of the electronic apparatus 301 is less than a preset value, the electronic apparatus 301 may output a first message for inquiring after the user in operation 703. The electronic apparatus 301 may display the first message and a graphic object for asking the user to respond, on a display. The electronic apparatus 301 may determine that the user is driving and may output the first message via voice. For example, the electronic apparatus 301 may output a message to the user via voice "I am OK".

Upon receiving a user input as a response result to the first message, the electronic apparatus 301 may output the second message in operation 704. The second message may include information for asking the user to perform an operation. The second message may include a plurality of questions. An output type and information of the second message are the same as in the description given with reference to FIGS. 4A and 4B and, thus, a detailed description thereof is omitted here.

Upon receiving a user input as a result of a response to the second message, the electronic apparatus 301 may search for the hospital 313 at the shortest distance based on a current position of the user and may output a position in operation 705. The electronic apparatus 301 may drive an application to provide information for allowing the user to arrive at the hospital 313. For example, upon determining that the user is driving, the electronic apparatus 301 may drive a navigation application, may set a position of the hospital 313 closest to a destination, and may provide information on a path to the hospital 313. Alternatively, the electronic apparatus 301 may provide information on the hospital 313 to a surrounding device (e.g., a navigation device present in a vehicle).

Although the electronic apparatus according to an exemplary embodiment of the present disclosure has been described with reference to limited and exemplary embodiments and drawings, the electronic apparatus according to an exemplary embodiment is not limited to the above exemplary embodiment and may be changed and modified in various ways from the description by one of ordinary skill in the art to which the electronic apparatus pertains.

Accordingly, embodiments stated in the present specification are proposed for description and understanding of disclosed technological features and do not limit the scope of the technology stated in the present specification. Accordingly, the scope of the present specification needs to be interpreted as including all modifications or other various exemplary embodiments based on the technological ideas of the present specification.

FIG. 1
101 COMMUNICATOR
103 CONTROLLER
105 SENSOR
107 INPUTTER
109 OUTPUTTER

FIG. 2
210 CONTROLLER
220 COMMUNICATOR
221 CELLULAR MODULE
223 WIFI MODULE
225 BT MODULE
227 GNSS MODULE
228 NFC MODULE
229 RF MODULE
224 SUBSCRIBER IDENTIFICATION MODULE
230 MEMORY
232 EMBEDDED MEMORY
234 EXTERNAL MEMORY
240 SENSOR
240A GESTURE SENSOR
240B GYRO SENSOR
240C BAROMETER
240D MAGNETIC SENSOR
240E ACCELERATION SENSOR
240F GRIP SENSOR
240G PROXIMITY SENSOR
240H RGB SENSOR
240I MEDICAL SENSOR
240J TEMPERATURE-HUMIDITY SENSOR
240K ILLUMINANCE SENSOR
240M UV SENSOR
240N ULTRASONIC SENSOR
250 INPUTTER
252 TOUCH PANEL
254 PEN SENSOR
256 KEY
258 ULTRASONIC INPUT DEVICE
260 DISPLAY
262 PANEL
264 HOLOGRAM DEVICE
266 PROJECTOR
270 INTERFACE
276 OPTICAL INTERFACE
280 AUDIO MODULE
282 SPEAKER
284 RECEIVER
286 EARPHONE
288 MICROPHONE

291 CAMERA MODULE
295 POWER MANAGEMENT MODULE
296 BATTERY
297 INDICATOR
298 VIBRATION DEVICE
FIG. 3
301 ELECTRONIC APPARATUS (WEARABLE)
302 ELECTRONIC APPARATUS (SMARTPHONE)
303 USER A
SMARTPHONE
305 USER C
SMARTPHONE
309 FAMILY SMARTPHONE
313 HOSPITAL
311 RESCUE CENTER
FIG. 4A
START
401 RECEIVE MEDICAL INFORMATION OF USER
403 SENSE MOVEMENT OF ELECTRONIC APPARATUS
405 OUTPUT MESSAGE FOR GUIDING SPECIFIC OPERATION TO USER OR TRANSMIT INFORMATION RELATED TO ELECTRONIC APPARATUS THROUGH COMMUNICATOR BASED ON MEDICAL INFORMATION AND MOVEMENT OF ELECTRONIC APPARATUS
END
FIG. 4B
START
431 RECEIVE MEDICAL INFORMATION OF USER
433 SENSE MOVEMENT OF ELECTRONIC APPARATUS
435 DETECT ABNORMAL SITUATION BASED ON MEDICAL INFORMATION OF USER
437 MOVEMENT FROM ELECTRONIC APPARATUS FOR PREDETERMINED PERIOD TIME DETECTED?
439 TRANSMIT POSITION INFORMATION TO SURROUNDING USER
441 SEARCH FOR RESCUE CENTER AT SHORTEST DISTANCE
443 TRANSMIT POSITION INFORMATION TO RETRIEVED RESCUE CENTER
445 OUTPUT FIRST MESSAGE (MESSAGE FOR INQUIRING AFTER)
447 RESPONSE FROM USER?
449 OUTPUT SECOND MESSAGE (MESSAGE FOR CHECKING USER STATE)
451 RESPONSE TO OUTPUT OF SECOND MESSAGE?
453 DETERMINE WHETHER USER IS POTENTIALLY ABNORMAL BASED ON RESPONSE RESULT
455 POTENTIALLY ABNORMAL?
457 SEARCH CLOSE HOSPITAL AND PROVIDE POSITION INFORMATION OF CLOSE HOSPITAL
459 TRANSMIT POSITION INFORMATION TO SURROUNDING USER
461 OUTPUT THIRD MESSAGE (MESSAGE FOR GUIDING STABILITY OF USER_
END
FIG. 5
503 ARE YOU OK?
505 RAISE RIGHT HAND UP ON YOUR HEAD
507 FOLD THUMB
FIG. 7
703 ARE YOU OK?
704 RAISE HAND WITH WEARABLE DEVICE THEREON

What is claimed is:

1. An electronic apparatus comprising:
a plurality of sensors including a first sensor configured to sense movement of the electronic apparatus and a second sensor configured to sense position of the electronic apparatus;
a communication circuit;
an input device;
an output device; and
a processor configured to:
obtain medical information of a user;
detect an abnormal state of the user based on the medical information; and
based on detecting the abnormal state of the user:
obtain movement information from the first sensor indicative of aspects of movement of the electronic apparatus;
based on the movement information indicating movement of the electronic apparatus within a first period of time:
control the output device to output to the user a first message;
based on receiving a response to the first message from the user within a second period of time, control the output device to output to the user a second message; and
based on receiving no response to the first message from the user within the second period of time, control the communication circuit to transmit information including position information of the electronic apparatus obtained from the second sensor to a first external device, and
based on the movement information indicating no movement of the electronic apparatus within the first period of time, control the communication circuit to transmit the information including the position information to a second external device,
wherein the first message prompts the user to perform a movement, and the second message comprises one or more questions for checking a user state.

2. The electronic apparatus as claimed in claim 1, wherein the processor is configured to obtain the medical information of the user based on a signal output from a third sensor.

3. The electronic apparatus as claimed in claim 1, wherein the processor is configured to control the communication circuit to obtain the medical information from a third external device.

4. The electronic apparatus as claimed in claim 1, wherein the transmitted information further includes a message indicating an emergency of the user.

5. The electronic apparatus as claimed in claim 4, wherein the communication circuit includes a short distance communication circuit, and wherein the transmitted information is transmitted through the short distance communication circuit.

6. The electronic apparatus as claimed in claim 4, wherein the processor is configured to determine a position to which the transmitted information is to be transmitted, based on the position information, and controls the communication circuit to transmit the message to the position.

7. The electronic apparatus as claimed in claim 1, wherein the output device includes a display and the processor is configured to control the display to display at least one of the first message or the second message.

8. The electronic apparatus as claimed in claim 1, wherein the output device includes a speaker and the processor is configured to control the speaker to output at least one of the first message or the second message.

9. The electronic apparatus as claimed in claim 1, wherein the medical information includes at least one of a heart rate, a pulse rate, body temperature, or blood pressure.

10. The electronic apparatus as claimed in claim 1, wherein the plurality of sensors includes an altitude sensor and the processor is configured to obtain an altitude of the electronic apparatus based on a signal output from the altitude sensor and the abnormal state of the user is based on a variation per unit time of the altitude being greater than a variation value.

11. The electronic apparatus as claimed in claim 1, wherein the movement prompted by the first message is movement of the electronic apparatus.

12. The electronic apparatus as claimed in claim 1, wherein the first message comprises a message for guiding the user to perform the movement.

13. The electronic apparatus as claimed in claim 1, further comprising a microphone,
wherein the processor is configured to determine whether the user is in an emergency based on voice input through the microphone.

14. The electronic apparatus as claimed in claim 1, wherein the processor is configured to identify whether a response to the first message from the user is received based on movement information obtained from the first sensor after the first message is output.

15. A method of controlling an electronic apparatus, the method comprising:
obtaining medical information of a user;
detecting an abnormal state of the user based on the medical information; and
based on detecting the abnormal state of the user:
obtaining, from a first sensor of the electronic apparatus, movement information indicating movement of the electronic apparatus,
wherein the movement is within a first period of time;
in response to obtaining the movement information indicating the movement within the first period of time, outputting, via an output device of the electronic apparatus, a first message;
receiving a response to the first message from the user within a second period of time; and
in response to receiving the response to the first message, outputting to the user a second message.

16. A non-transitory computer-readable storage medium storing a program which, when executed by a processor of an electronic apparatus, causes the processor to control the electronic apparatus to perform operations comprising:
obtaining medical information of a user;
detecting an abnormal state of the user based on the medical information; and
based on detecting the abnormal state of the user:
obtaining, from a first sensor of the electronic apparatus, movement information indicating movement of the electronic apparatus;
based on the movement information indicating movement of the electronic apparatus within a first period of time:
outputting, via an output device of the electronic apparatus, a first message;
based on receiving a response to the first message from the user within a second period of time, outputting to the user a second message; and
based on receiving no response to the first message from the user within the second period of time, transmitting information including position information of the electronic apparatus obtained from a second sensor to a first external device, and
based on the movement information indicating no movement of the electronic apparatus within the first period of time, transmitting the information including the position information to a second external device,
wherein the first message prompts the user to perform a movement, and the second message comprises one or more questions for checking a user state.

* * * * *